United States Patent [19]
Cascio et al.

[11] Patent Number: 5,213,210
[45] Date of Patent: May 25, 1993

[54] EASY-LOADING SUTURE PACKAGE

[75] Inventors: Jack Cascio, Bridgewater; Konstantin Ivanov, Dunellen; Marvin Alpern, Glen Ridge, all of N.J.; Robert Cerwin, Pipersville, Pa.; Joseph Siernos, Whitehouse Station; Martin Sobel, Flemington, both of N.J.

[73] Assignee: Ethicon, Inc., Somerville, N.J.

[21] Appl. No.: 843,651

[22] Filed: Feb. 28, 1992

[51] Int. Cl.⁵ .............................................. A61B 17/06
[52] U.S. Cl. .................................... 206/380; 206/63.3
[58] Field of Search .................... 206/63.3, 380, 409, 206/338, 339, 480, 495

[56] References Cited

U.S. PATENT DOCUMENTS

| | | | |
|---|---|---|---|
| 3,338,401 | 8/1967 | Regan, Jr. | 206/63.3 |
| 3,972,418 | 8/1976 | Schuler et al. | 206/63.3 |
| 4,424,898 | 1/1984 | Thyen et al. | 206/63.3 |
| 4,961,498 | 10/1990 | Kalinski et al. | 206/339 |
| 4,967,902 | 11/1990 | Sobel et al. | 206/63.3 |
| 5,052,551 | 10/1991 | Cerwin et al. | 206/63.3 |
| 5,056,658 | 10/1991 | Sobel et al. | 206/63.3 |
| 5,099,994 | 3/1992 | Kalinski et al. | 206/63.3 X |
| 5,131,533 | 7/1992 | Alpern | 206/380 X |

Primary Examiner—Steven N. Meyers
Assistant Examiner—Jacob K. Ackun, Jr.
Attorney, Agent, or Firm—Emil Richard Skula

[57] ABSTRACT

An easy loading suture package contains sutures in a channel near the periphery of the package. Resilient cantilevered fingers extend most of the way across the channel to prevent any part of the suture from coming up out of the channel either during or after loading of the suture into the package. A needle park retains a needle attached to one end of the suture. The package lends itself to fabrication by molding and is adapted for automated loading and convenient, reliable dispensing.

11 Claims, 5 Drawing Sheets

EASY-LOADING SUTURE PACKAGE

BACKGROUND OF THE INVENTION

1. Field of the Invention

This invention relates to a suture package designed to facilitate automated loading of a needle and suture into the package.

2. Description of the Related Art

As is the case with many articles of manufacture, the requirements of the user of a surgical needle and suture —a surgeon or other health professional—limit the flexibility of the manufacturer. The goal is to design a package that meets the surgeon's requirements, while still being easy and inexpensive to manufacture.

In the packaging of surgical needles and sutures, it is important that the needle and its attached suture be easily removable from the package in one smooth motion. When the needle is grasped by a forceps and pulled, the needle should easily release from the package, and the suture should withdraw from the package smoothly, without binding or snagging in the package, and without becoming entangled. Also, suture materials, particularly monofilaments such as catgut, polydioxanone and the like, especially the heavier deniers, are known to take a set during storage; i.e., they tend to have a "memory" causing them to retain the shape of their position in the package after removal from the package. Hence, the package should be designed to eliminate any tight bends or curves required in order to package the suture.

One type of suture package that generally meets the requirement that sutures be easily removable is the "oval wrap" suture package. Oval wrap suture packages have been disclosed in U.S. Pat. Nos. 4,961,498, issued Oct. 9, 1990 to Kalinski et al.; 4,967,902, issued Nov. 6, 1990 to Sobel et al.; and U.S. Pat. No. 5,052,551, issued Oct. 1, 1991 to Cerwin et al. These packages include a structure to hold (or "park") a needle and an oval ("racetrack-shaped") channel for retaining a suture that is attached to the needle. While these suture packages are well-adapted to meet the requirements of the user, they are not ideally suited for inexpensive and automated manufacturing.

SUMMARY OF THE INVENTION

In accordance with the present invention, a package for retaining a wound suture and attached needle comprises:
 a) a base,
 b) an inner and outer wall on the base, defining a channel for containing the suture, the outer wall being substantially around the periphery of the base and the inner wall having an opening to permit a first end of the suture to emerge from the channel,
 c) a plurality of resilient cantilevered retaining fingers extending over the channel for preventing the suture from lifting up out of the channel, and
 d) a needle park to retain adjacent to the base a needle attached to the first end of the suture.

The package lends itself to inexpensive manufacture, high-speed automated loading, and convenient reliable dispensing of the needle and suture.

When compared with suture packages of the prior art that used doors that were closed over the suture channel (such as the package of U.S. Pat. No. 4,967,902), the present package provides several advantages. When molded in a single piece, the doors extend beyond the outer perimeter of the package, thus taking up a larger area and reducing the number of packages that can be produced in a mold of a given area. Molding of the present package is more reliable and less expensive, because there is no need for the thin "living" hinges, where the doors attach to the package perimeter. In addition, suture dispensing is more reliable, because there is no risk that the emerging suture will get caught in a door or door latch.

BRIEF DESCRIPTION OF THE DRAWINGS

FIG. 2A is a view of a part of an alternative embodiment of the package of FIG. 2.

DETAILED DESCRIPTION OF THE INVENTION

Figure 1:
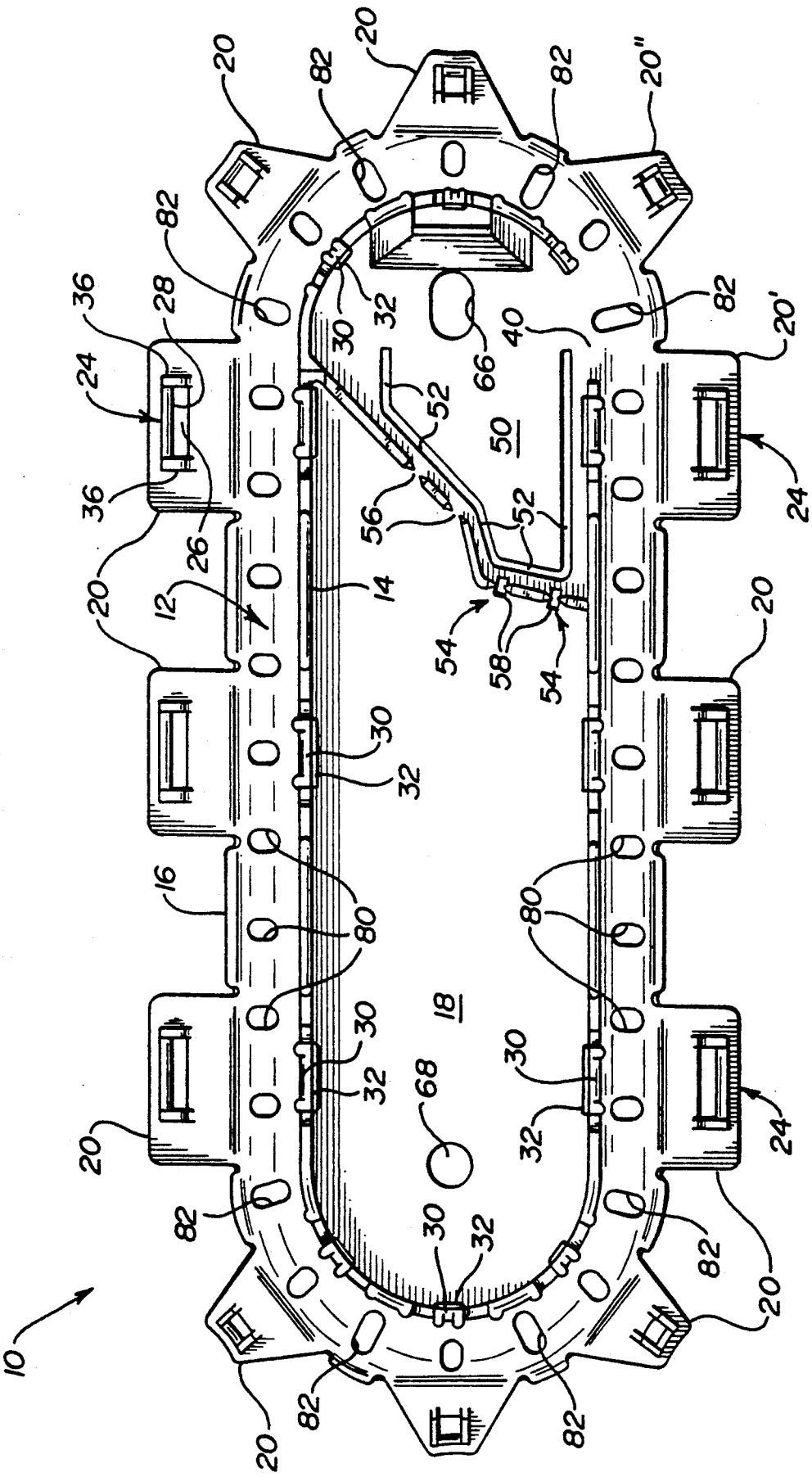
FIG. 1 is a plan view of a suture package of the prior art.

The present invention can best be understood by first considering a suture package of the prior art. Such a package is depicted in FIG. 1. The package 10 includes a central floor area 18 which is surrounded by an oval channel 12 having two opposing straight sections connected by two semicircular end sections. The channel is defined by an inner wall 14 which extends upwardly from the floor area. Portions of the door locking means are formed at intervals about the inner wall 14. The bottom and outer periphery of the channel 12 is defined by a curved section 16 of the package, which extends outwardly form the inner wall 14 at the level of the floor 18 and curves upwardly to approximately the elevation of the inner wall 14. Attached at the outer periphery of the curved section 16 are a plurality of hinged doors 20. The doors are hinged at an elevation which is slightly below the uppermost elevation of the outer periphery of the curved section and the inner wall so that, when the doors are folded over the channel and latched in place, the upper surfaces of the doors will align with the upper elevation of the outer periphery and inner wall. Formed in each door is a portion of the door locking means 24, including a latch opening 26 bounded by a door latch projection 28 and two fins 36. When the door is closed over channel 12, the top of the latch post 30 engages the door latch opening 26 and the door latch projection 28 hooks around the latch post projection 32 to lock the door in the closed position.

Located inside the oval channel is a needle park, including undercut and rigid needle holders 54 and 56, respectively. The package floor beneath needle holder 54 has been undercut by removal of the floor area indicated at 58, which enables the tapered ends of the overlying needle holder to flex and bend somewhat when a needle is inserted in the wall opening. Thus, the undercut needle holder 54 can accommodate a wider range of needle gauges than the rigid needle holder 56 can accommodate. Adjacent the needle park is a relief flap 50 defined by a cutout 52. A portion of the inner wall 14 is eliminated in the vicinity of the needle park to form an opening 40 in the channel wall through which the suture of the needle accesses the channel 12 between doors 20' and 20".

The bottom of the channel 12 formed by the curved section 16 is periodically perforated by holes 80 and 82 around the circumference of the channel. These holes are used for assembling the package with a suture and needle as follows: Package 10 is placed on an assembly platform that has a number of upwardly extending pins. Two of the pins are aligned to extend upward through holes 66 and 68 in the center of the package to retain the package in its assembly position on the platform. Eight other pins extend upward and are aligned to pass through the holes 82 of the channel. The platform is open beneath the remaining channel holes 80, and a vacuum source below the platform draws air through the holes 80. With the package so emplaced, the needle is located in the needle holder and the suture is looped above the pin extending through hole 66 then downward through the vent 40 and into the channel. The suture is then wound in a clockwise direction around the pins which extend through the channel holes 82. The size and positioning of the pins is such that the suture is loosely positioned in the center of the channel 12, after the pins are withdrawn from the holes. As the suture is wound around the pins, the flow of air through the holes 80 draws the suture down into the channel. With the suture completely wound in the channel, the doors are folded closed and latched to the latch posts of the inner channel wall. The pins are then withdrawn from the holes 66, 68 and 82 and air flow through holes 80 is stopped.

Additional details regarding the construction of the suture package of FIG. 1 appear in U.S. Pat. No. 4,967,902, incorporated herein by reference.

Figure 2:
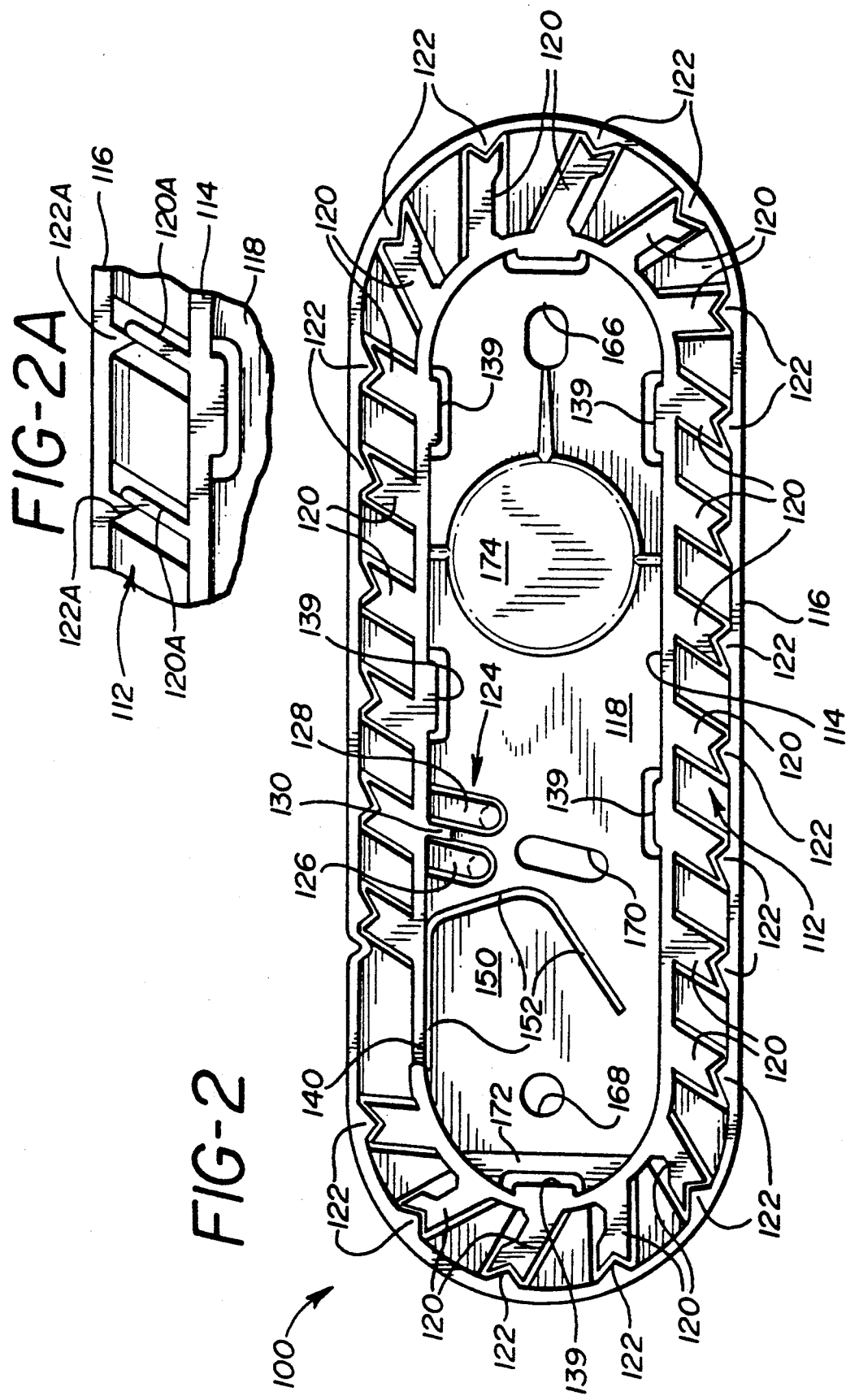
FIG. 2 is a plan view of a suture package of the present invention.

FIG. 2 depicts an oval wrap suture package of the present invention. Package 100 has several differences from the package of FIG. 1, as well as some similarities. Central floor area 118 is surrounded by an oval channel 112 that is defined by an inner wall 114 and an outer wall 116, which both extend up from the floor area. In place of the doors (20) to prevent a suture from lifting up out of the channel, cantilevered fingers 120 extend from the top of inner wall 114 most of the way across channel 112. In the embodiment shown, optional nibs 122, one for each finger 120, extend from outer wall 116, to leave a small gap between each finger and the corresponding nib. Note that the facing ends of a finger 120 and nib 122 preferably overlap in the longitudinal direction to reduce the likelihood of suture escape. Thus, in the embodiment shown the gap is chevron-shaped, but other suitable gap shapes will be apparent to a person of ordinary skill in the art. Furthermore, there need be no gap at all between the fingers and nibs. Such an embodiment is shown in FIG. 2A, which shows fingers 120A and nibs 122A, alternatives to the fingers 120 and nibs 122 depicted in FIG. 2.

Needle park 124 comprises cantilevered arms 126 and 128, which extend horizontally above the base and optional stop 130. The elevation of arms 126 and 128 above the base and their mechanical properties are chosen to permit them to hold needles of the desired range of gauges. Adjacent to needle park 124, relief flap 150 is defined by cutout 152. The height of inner wall 114 is reduced (or the wall is eliminated) along part of its length to form opening 140, through which the suture can pass into channel 112.

Three holes in the base are used during loading a needle and suture into the package. The package is supported on an assembly platform during the loading process by pins that extend upward through holes 166 and 168. Thus supported, a needle is placed on the base near needle park 124 and is then pushed into place near or against stop 130 by an "L" shaped bar that extends up through hole 170. Note that this needle-loading method does not require that the needle be precisely positioned on the base, before it is pushed into place. The attached suture is then looped about the pin that extends through hole 168 and passed through opening 140 into channel 112. The suture is wound into channel 112 by successively raising the free end of each finger 120 just before the suture is placed and permitting the finger to spring back into place immediately thereafter. The element that raises finger 120 can also protect the suture from damage that might otherwise be caused when the suture rubs against nibs 122 or other package surfaces during loading. (When the embodiment of FIG. 2A is used, finger 120A is moved aside horizontally, rather than being raised.) By thus essentially eliminating the time during which the suture lies uncovered in the channel, there is no need to use a vacuum hold-down to contain the suture, and the package is suitable for holding either monofilament or braided sutures of a wide variety of compositions and mechanical properties. The package design preferably provides close spacing of the fingers so that the end or "tail" of the suture is likewise contained in the channel.

Figure 3:
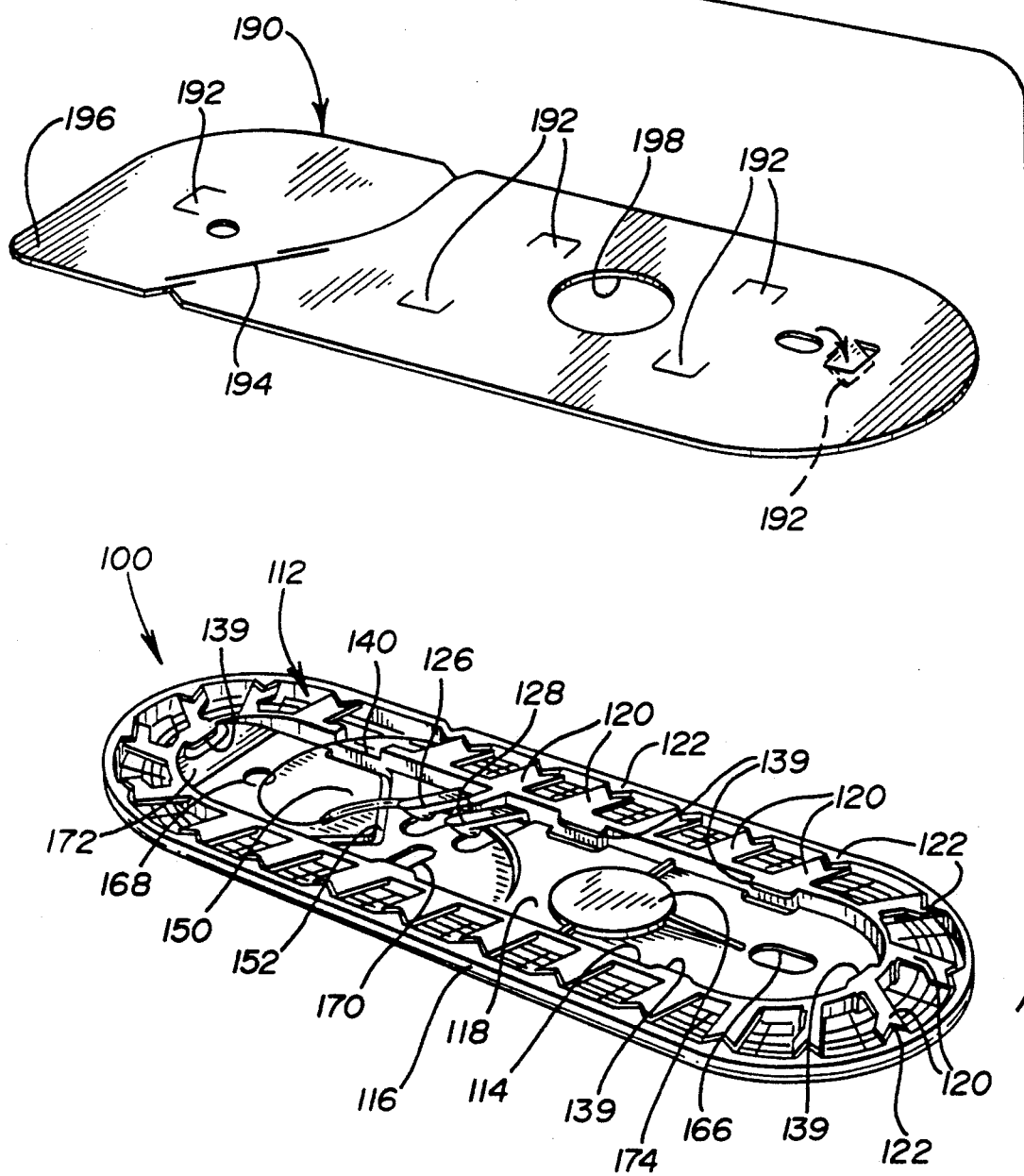
FIG. 3 is an assembly drawing of the suture package of FIG. 2.

When winding is complete, the pins are withdrawn from holes 166 and 168 and paper cover 190 is placed over the package, as shown in FIG. 3, to protect the needle and suture. The cover 190 includes a scored tear line 194 along which the cover will preferentially tear when it is grasped at the tear corner 196 for opening. The cover 190 also includes a plurality of perforated pushout tabs 192. The tabs are located so as to be in alignment with corresponding projections 139 that extend from inner wall 114. When the tabs are pressed downward, the outer edges of the tabs snap under the overhanging edges of the projections with which they are aligned, retaining the cover in place on the package 100. Cover 190 also includes a hole 198 that lines up with a circular landing 174 that rises from floor 118. Hole 198 permits a vacuum holder to attach to landing 174 to facilitate moving the package after cover 190 is in place and also permits alcohol to be introduced onto the landing (and into the package) for those products sold wet with alcohol. With cover 190 in place, the suture package is ready for final packaging, which comprises hermetically sealing the package in foil (for absorbable sutures, which require a foil barrier) or sealing it in a thermoformed film blister (for non-absorbable sutures).

A non-foil package is opened by first removing the film blister. Then the user grasps tear corner 196 and tears the cover 190 downward, causing the cover to open along scored tear line 194. When a foil package (not shown) is to be opened, the user grasps a tear notch of the package and tears the foil and cover downward, causing the foil package to open along scored tear line 194. With either package, this process reveals that portion of the package to the left of needle park 124, with the point of the needle still protected by the cover to the right of the needle park.

Figure 4:
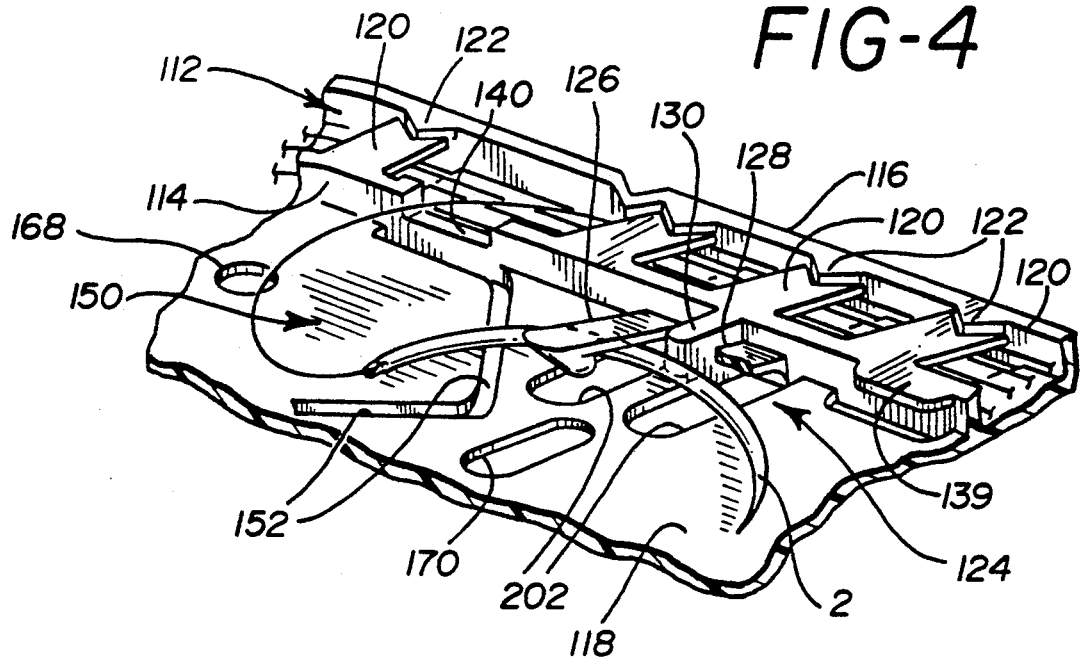
FIG. 4 is a perspective view of a needle park.

FIG. 4 depicts needle park 124, with curved needle 2 held against package floor 118 by cantilevered arms 126 and 128 (partially cut away). For clarity, cover 190 is not shown. When needle 2 is to be removed, the user grasps the needle with a forceps. Since the needle is resting flush with the floor of the package, making it difficult to securely grasp the needle with the tip of the forceps, the relief flap 150 is provided. As the user presses the tip of the forceps against the relief flap, the flap gives way and bends away from the needle, thereby enabling the user to pass the tip of the forceps beyond the needle. The needle may then be securely grasped in the tip of the forceps and removed from the needle holder. Optional stop 130 keeps the needle away form wall 114 to facilitate grasping the needle. Inclined floor section 172 facilitates removing the needle from the package without hangup.

Figure 5:
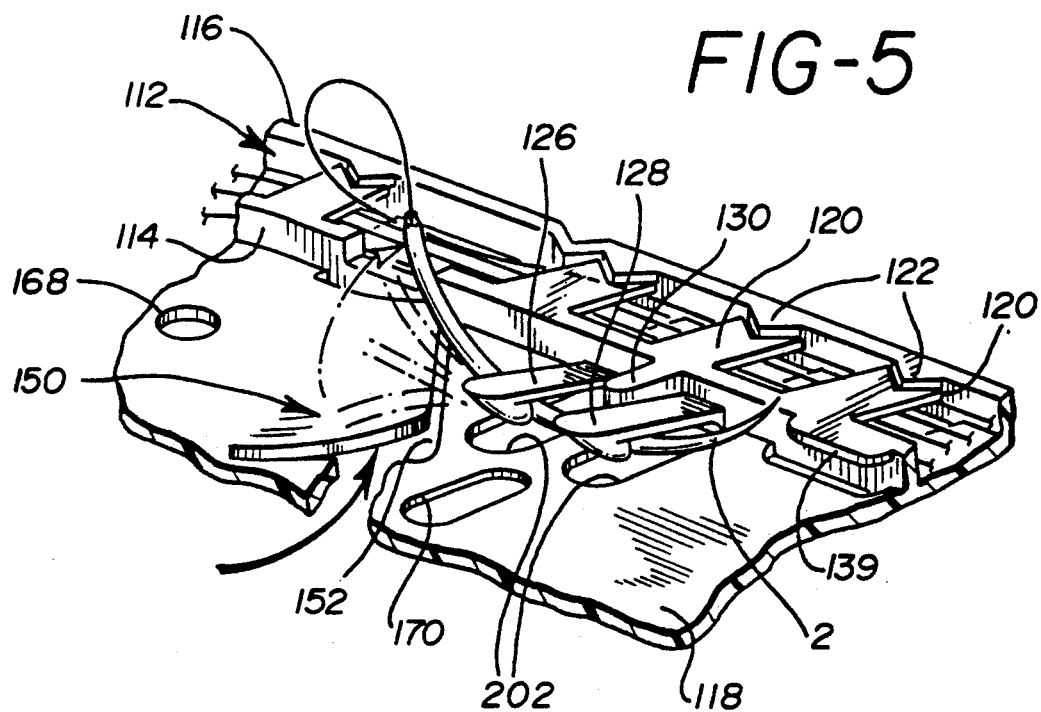
FIG. 5 illustrates a needle-removing mechanism.

Flap 150 also provides a means to grasp the needle in another way. If cover 190 has been removed, then the ends of the needle can be rotated into an upright position simply by pushing against the underside of flap 150 (as shown in FIG. 5). The needle can then be easily grasped by forceps or fingers.

Figure 6:
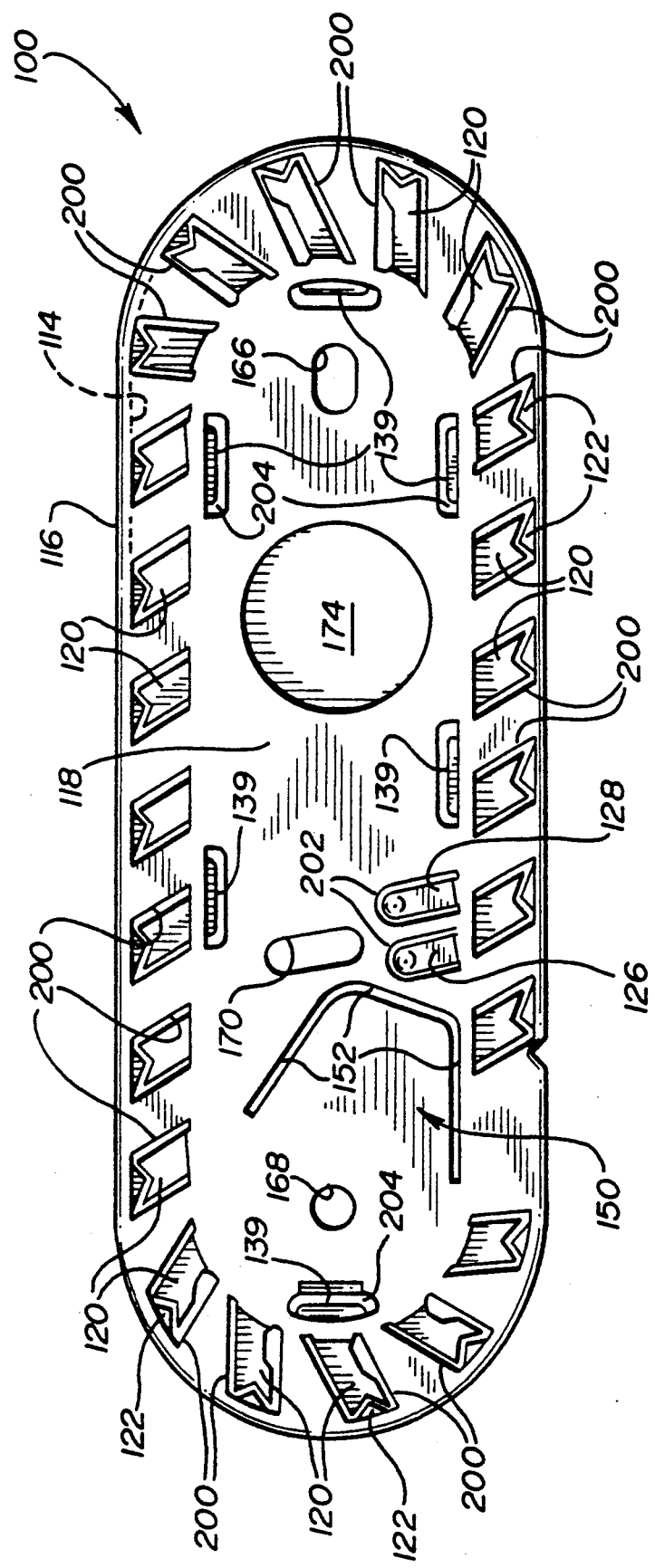
FIG. 6 is a plan view of the bottom of a suture package.

Package 100 may be fabricated from any of a number of materials; however, molded thermoplastics are preferred, because they permit low cost and high precision. Molding places some constraints on the package structure, however. As shown in FIG. 6, a plan view of the package bottom, if the package is molded, the base preferably has spaced apart holes 200 that correspond to the cantilevered fingers 120. Similarly, it has holes 202 to correspond to cantilevered arms 126 and 128 and holes 204 to correspond to projections 139. Holes 200, 202, and 204 facilitate molding package 100 in a single piece. Molding also puts limits on how closely elements can be spaced for reliable fabrication. Thus, spacing between fingers is preferably at least about 2.3 mm, which is small enough to contain the suture tail, particularly on the straight sections of the package. Preferably, package dimensions are selected so that suture tails will always fall within the straight sections, in which case a single finger suffices to retain the multiple strands at each round end of the package. The embodiment of FIG. 2 is suitable for containing sutures of random lengths.

Desirable characteristics for the package material include slipperiness, to facilitate dispensing the suture; hardness, so the suture doesn't become embedded in the surface; and dissimilarity to suture composition, to avoid the binding that occurs between elements of the same composition in contact. Suitable thermoplastics include polyester, polyvinyl chloride, polypropylene, polystyrene, and polyethylene. The best combination of desirable properties is provided by polypropylene or high-density polyethylene.

We claim:

1. A package for retaining a wound suture and attached needle comprising:
    a) a base,
    b) an inner and outer wall on the base, defining a channel for containing the suture, the outer wall being substantially around the periphery of the base and the inner wall having an opening to permit a first end of the suture to emerge from the channel,
    c) a plurality of resilient cantilevered retaining fingers non-movably attached at one end of each said fingers to one of said walls and extending over the channel for preventing the suture from lifting up out of the channel, and
    d) a needle park to retain adjacent to the base a needle attached to the first end of the suture.

2. The package of claim 1 in which the package comprises a molded thermoplastic material.

3. The package of claim 2 in which the base has a plurality of spaced-apart openings corresponding to the retaining fingers.

4. The package of claim 3 in which the package comprises a single molded piece.

5. The package of claim 2 in which the thermoplastic material is selected form the group consisting of polyester, polyvinyl chloride, polypropylene, polystyrene, and polyethylene.

6. The package of claim 5 in which the thermoplastic material is polypropylene or high-density polyethylene.

7. The package of claim 1 in which the retaining fingers extend from the top of the inner wall most of the way across the channel toward the outer wall.

8. The package of claim 1 further comprising a plurality of nibs, each corresponding to a retaining finger and extending from the outer wall toward the inner wall.

9. The package of claim 8 in which there is a chevron-shaped gap between each nib and its corresponding retaining finger.

10. The package of claim 1 in which the needle park comprises a plurality of cantilevered, spaced-apart arms above the base.

11. The package of claim 10, further comprising a cutout in the base to permit a section of the base to be tilted up or down.

* * * * *